(12) United States Patent
Seifert

(10) Patent No.: US 9,655,746 B2
(45) Date of Patent: May 23, 2017

(54) INTERVERTEBRAL SPINAL IMPLANT

(75) Inventor: Jody L. Seifert, Birdsboro, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 333 days.

(21) Appl. No.: 13/292,316

(22) Filed: Nov. 9, 2011

(65) Prior Publication Data

US 2013/0116790 A1  May 9, 2013

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3082* (2013.01); *A61F 2002/30266* (2013.01); *A61F 2002/30774* (2013.01); *A61F 2002/30836* (2013.01); *A61F 2002/30841* (2013.01); *A61F 2002/30843* (2013.01); *A61F 2002/4475* (2013.01); *A61F 2002/4622* (2013.01); *A61F 2002/4627* (2013.01); *A61F 2002/4629* (2013.01)

(58) Field of Classification Search
CPC ............................... A61F 2/442; A61F 2/4611
USPC .................... 623/17.11, 17.16; 606/86 A, 99
See application file for complete search history.

(56) References Cited

U.S. PATENT DOCUMENTS

| | | | |
|---|---|---|---|
| 6,258,125 B1 | 7/2001 | Paul | |
| 6,471,725 B1 | 10/2002 | Ralph | |
| 6,964,687 B1 | 11/2005 | Bernard | |
| 7,137,997 B2 * | 11/2006 | Paul | 623/17.11 |
| 7,331,996 B2 | 2/2008 | Sato | |
| 7,918,891 B1 | 4/2011 | Curran et al. | |
| 2006/0195190 A1 | 8/2006 | Lechmann | |
| 2007/0027544 A1 | 2/2007 | Mccord | |
| 2007/0260320 A1 * | 11/2007 | Peterman et al. | 623/17.16 |
| 2008/0077247 A1 * | 3/2008 | Murillo et al. | 623/17.16 |
| 2010/0228296 A1 | 9/2010 | Vraney | |
| 2010/0262249 A1 | 10/2010 | Peterman | |

* cited by examiner

*Primary Examiner* — David Isabella
*Assistant Examiner* — Christine Nelson

(57) ABSTRACT

An intervertebral implant for implantation in a treated area of an intervertebral space between vertebral bodies of a spine is provided. The upper surface and the lower surface of the implant each have a contact area capable of engaging with anatomy in the treated area, and the upper and lower surfaces define a through-hole having an inner surface extending through the spacer body. A first and second sidewalls extend from a front end and a back end, wherein the first and second sidewalls are configured with engagement portions positioned in close proximity to the front end and the back end. The front end and the back end are configured with a threaded hole for receiving an instrument for inserting the intervertebral implant into the intervertebral disc space.

17 Claims, 2 Drawing Sheets

INTERVERTEBRAL SPINAL IMPLANT

FIELD OF THE INVENTION

The present disclosure generally relates to a fixation device for positioning and immobilizing at least two adjacent vertebrae. In particular, the present invention relates to an interbody fusion device for implementation in the spine.

BACKGROUND OF THE INVENTION

The spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth. There is a need for an implant that can be inserted laterally into the vertebral disc space between adjacent vertebrae.

SUMMARY OF THE INVENTION

An intervertebral implant for implantation in a treated area of an intervertebral space between vertebral bodies of a spine is provided. The upper surface and the lower surface of the implant each have a contact area capable of engaging with anatomy in the treated area, and the upper and lower surfaces define a through-hole having an inner surface extending through the spacer body. A first and second sidewalls extend from a front end and a back end, wherein the first and second sidewalls are configured with engagement portions positioned in close proximity to the front end and the back end. The front end and the back end are configured with a threaded hole for receiving an instrument for inserting the intervertebral implant into the intervertebral disc space. The intervertebral implant can be comprised of metal. The intervertebral implant can also be comprised of PEEK.

DETAILED DESCRIPTION OF THE ILLUSTRATED EMBODIMENTS

Embodiments of the disclosure are generally directed to an intervertebral implant for use with the anterior, anterolateral, lateral, and/or posterior portions of at least one motion segment unit of the spine. The systems of the invention are designed to be conformable to the spinal anatomy, so as to be generally less intrusive to surrounding tissue and vasculature than existing implants.

Figure 1:
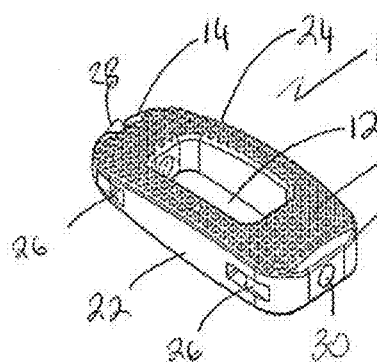
FIG. 1 is a perspective view of one embodiment of an intervertebral implant according to the present invention.
Figure 2:
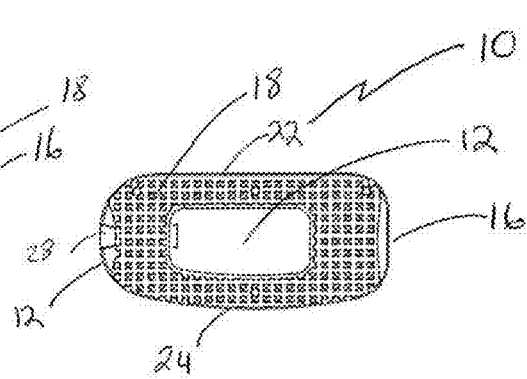
FIG. 2 is a top view of the intervertebral implant.
Figure 3:
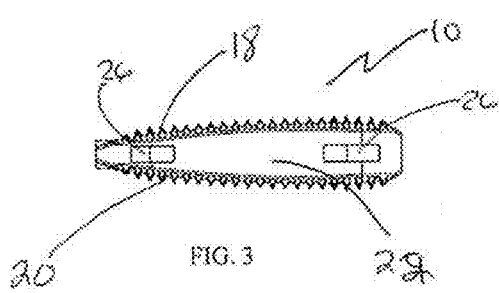
FIGS. 3 and 4 are side views of the intervertebral implant.
Figure 4:
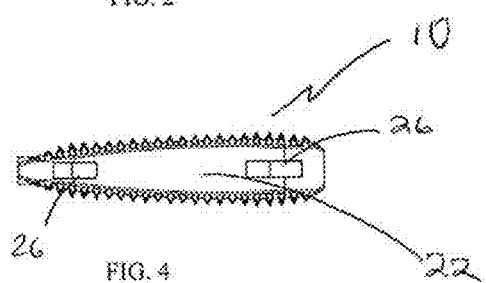
Figure 5:
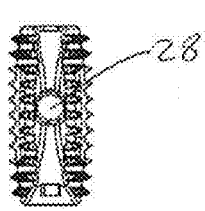
FIGS. 5 and 6 are front and back views of the intervertebral implant.
Figure 6:
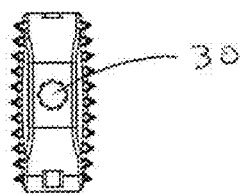

Referring now to FIGS. 1-6 one embodiment of a lateral intervertebral implant is shown. FIG. 1 is a perspective view of the implant according to the present invention. FIG. 2 illustrates a top view of the implant 10. As illustrated, the implant 10 is substantially rectangular with a hollow interior portion 12. The implant 10 is configured with a tapered front end 14 and a rectangular back end 16, as shown in FIGS. 3 and 4 which illustrate the side views of the implant 10. The implant 10 has an upper surface 18 and a parallel lower surface 20. The two side walls 22 and 24 are parallel to one another that extend from the back end 16 to the front end 14. The side walls 22 and 24 are configured with instrument attachment portions 26 near the front end 14 and the back end 16. The front end 14 and the back end 16 of the implant 10 are provided with a hole and/or aperture 28 and 30 for receiving an instrument that is used for inserting the implant 10. The implant 10 is coronally angled and allows for a surgeon to place the implant from the lateral approach regardless of the side of the access or direction of a scoliotic curve.

Figure 7:
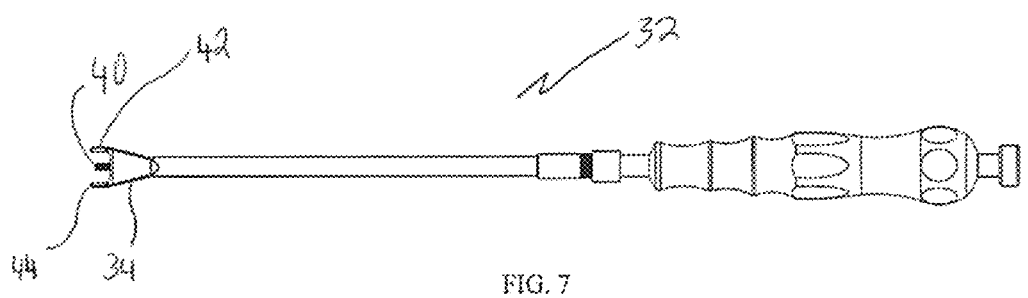
FIG. 7 is the instrument for engaging with the intervertebral implant during insertion.
Figure 8:
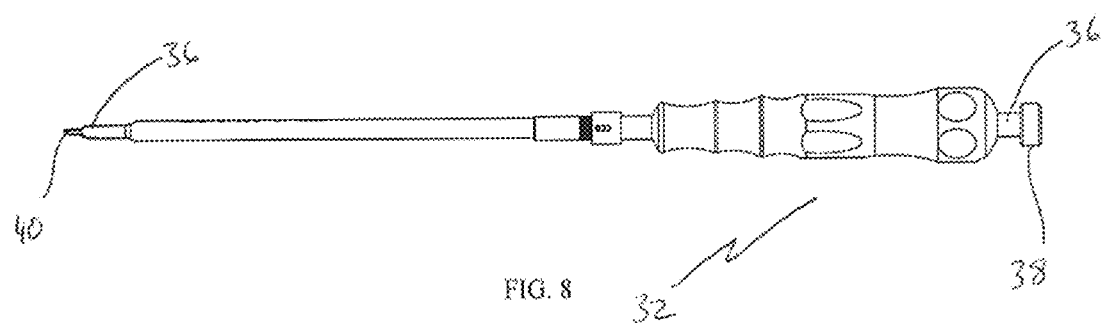
FIG. 8 is the threaded instrument for engaging with the intervertebral implant according to the present invention.

FIGS. 7 and 8 more clearly illustrates the instrument used for inserting the implant 10 into the intervertebral disc space. The instrument 32 comprises a substantially hollow tubular structure 34 having an internal rod 36 which is configured with a turning knob 38 at one end and a threaded portion 40 at the other end for threadeably engaging the threaded opening of the implant 10. The instrument 32 is configured with two extended arms 42 and 44 that engage with the attachment portions 26 of the implant. The implant is provided with attachment portions on the side walls of the front end and the back end so that the implant may be inserted in either direction. The internal rod 36 can be threaded into the back end of the implant or the front end depending on the surgeon's preference.

Bone graft and other bone material may be packed within the hollow portion of the implant which serves to promote bone ingrowth between the implant and the adjacent vertebrae. Once the bone ingrowth occurs, the implant will be a permanent fixture preventing dislodgement of the implant as well as preventing any movement between the adjacent vertebrae.

The implant 10 is also provided with a plurality of teeth projections extending form the upper and lower surfaces of the implant 10. Although the present implant illustrates teeth projections on the upper and lower surface, any type of projections may be utilized such as ridges. These projections prevent the implant from moving between the vertebrae, thus preventing movement of the implant prior to fusion.

Referring now to FIGS. 1-8, the method of inserting the implant 10 is described as follows. First, the threaded end of the internal rod of the instrument 32 is attached to the threaded opening of the implant by turning of the knob. Once the engaging end is in place, the extended arms 42 and 44 engage with attachment portions on the sidewalls of the implant. The implant is then placed at the entrance of the disc space between the two adjacent vertebrae. The knob is then tapped sufficiently hard enough the drive the implant into the disc space. It should be noted that the size of the implant is generally the same size as the disc space that is being replaced and can be either larger and/or smaller based on the intervertebral disc being removed.

While it is apparent that the invention disclosed herein is well calculated to fulfill the objects stated above, it will be appreciated that numerous modifications and embodiments may be devised by those skilled in the art.

What is claimed is:

1. An intervertebral implant for implantation in an intervertebral space between vertebrae, wherein said implant comprises:
    an upper surface and a lower surface wherein the upper and lower surfaces each have a contact area capable of engaging with adjacent vertebrae, and the upper and lower surfaces define a through-hole extending through the spacer body;
    first and second sidewalls extending from a front portion to a back portion and disposed in between the upper surface and the lower surface, wherein the first sidewall comprises a straight wall and the second sidewall comprises a convexly curved wall;
    the front portion being different from the back portion such that a profile of the front portion is tapered relative to a profile of the back portion, wherein the front portion and the back portion are each configured to be inserted into the intervertebral space between vertebrae such that the implant is insertable into the intervertebral space with the front portion or the back portion as a leading portion of insertion; and
    wherein the front portion is configured with a first threaded hole and the back portion is configured with a second threaded hole, each configured for receiving an instrument for inserting the intervertebral implant into the intervertebral disc space, wherein the implant is coronally angled,
    wherein the first sidewall includes a first engagement portion and a second engagement portion, wherein the first engagement portion is closer to the front portion than the back portion and the second engagement portion is closer to the back portion than the front portion, and wherein the first engagement portion does not extend into the front portion configured with the first threaded hole, and wherein, the first engagement portion is a first indentation into the first sidewall near the front portion and the second engagement portion is a second indentation into the first sidewall near the back portion, wherein the first and second indentations are substantially rectangular in shape and have a length greater than a height.

2. The intervertebral implant of claim 1, wherein the implant is comprised of metal.

3. The intervertebral implant of claim 1, wherein the implant is comprised of PEEK.

4. The intervertebral implant of claim 1, wherein the implant comprises a plurality of protrusions on the upper and lower surfaces of the implant.

5. The intervertebral implant of claim 1, wherein the second sidewall includes a third engagement portion and a fourth engagement portion.

6. The intervertebral implant of claim 5, wherein the third engagement portion is closer to the front portion than the back portion and the fourth engagement portion is closer to the back portion than the front portion, and wherein the third engagement portion does not extend into the front portion configured with the first threaded hole.

7. The intervertebral implant of claim 1, wherein the back portion of the implant is tapered.

8. The intervertebral implant of claim 1, wherein the first and second sidewalls are not textured.

9. The intervertebral implant of claim 1, wherein the first and second sidewalls are solid without openings therethrough.

10. The intervertebral implant of claim 1, wherein the first and second engagement portions are aligned with one another and extend longitudinally along a length of the first sidewall.

11. The intervertebral implant of claim 1, wherein the back portion is rectangular.

12. A spinal system for implantation in an intervertebral space between vertebral bodies of a spine, comprises:
    an intervertebral implant comprising:
        an upper surface and a lower surface wherein the upper and lower surfaces each have a contact area capable of engaging with verterbrae, and the upper and lower surfaces define a through-hole extending through the spacer body;
        first and second sidewalls extending from a front end and a back end and disposed in between the upper surface and the lower surface, wherein the first sidewall comprises a straight wall and the second sidewall comprises a convexly curved wall;
        the front end being different from the back end such that a profile of the front end is tapered relative to a profile of the back end, wherein the front end and the back end are each configured to be inserted into the intervertebral space between vertebrae such that the implant is insertable into the intervertebral space with the front end or the back end as a leading portion of insertion; and
    an instrument capable of engaging with the intervertebral implant in the front end or the back end,
    wherein the front end is configured with a first threaded hole and the back end is configured with a second threaded hole, each configured for receiving the instrument wherein the implant is angled,
    wherein the first sidewall includes a first engagement portion and a second engagement portion, wherein the first engagement portion is closer to the front end than the back end and the second engagement portion is closer to the back end than the front end, and wherein the first engagement portion does not extend into the front end configured with the first threaded hole, and wherein the first engagement portion is a first indentation into the first sidewall near the front portion and the second engagement portion is a second indentation into the first sidewall near the back portion, wherein the first and second indentations are substantially rectangular in shape and have a length greater than a height.

13. The intervertebral implant of claim 12, wherein the plate portion is comprised of metal.

14. The intervertebral implant of claim 12, wherein the intervertebral implant comprises a plurality of protrusions on the superior and inferior portions.

15. The intervertebral implant of claim 12, wherein the second sidewall includes a third engagement portion and a fourth engagement portion.

16. The intervertebral implant of claim 15, wherein the third engagement portion is closer to the front end than the back end and the fourth engagement portion is closer to the back end than the front end, and wherein the third engagement portion does not extend into the front end configured with the first threaded hole.

17. The intervertebral implant of claim 16, wherein the fourth engagement portion does not extend into the back end configured with the second threaded hole.

\* \* \* \* \*